United States Patent
Kiplinger et al.

(10) Patent No.: US 8,431,689 B2
(45) Date of Patent: Apr. 30, 2013

(54) METHOD OF SYNTHESIS OF ANHYDROUS THORIUM(IV) COMPLEXES

(75) Inventors: Jaqueline L. Kiplinger, Los Alamos, NM (US); Thibault Cantat, Issy les Moulineaux (FR)

(73) Assignee: Los Alamos National Security, LLC, Los Alamas, NM (US)

( * ) Notice: Subject to any disclaimer, the term of this patent is extended or adjusted under 35 U.S.C. 154(b) by 386 days.

(21) Appl. No.: 12/778,891

(22) Filed: May 12, 2010

(65) Prior Publication Data

US 2011/0282039 A1    Nov. 17, 2011

(51) Int. Cl.
C07F 5/00 (2006.01)
C01G 56/00 (2006.01)
C01F 15/00 (2006.01)

(52) U.S. Cl.
USPC .............. 534/11; 423/3; 423/11; 423/252

(58) Field of Classification Search ............ 534/11; 423/3, 11, 252
See application file for complete search history.

(56) References Cited

U.S. PATENT DOCUMENTS 5,166,324 A * 11/1992 Avens et al. ............... 534/11

OTHER PUBLICATIONS

Cantat et al., ChemComm, 2010, 46, p. 919-921.*
Arunachalampillai et al., Organometallics, 2006, 25, p. 3856-3866.*
Wilkerson et al., Inorg. Chem., 1999, 38, p. 4156-4158.*
Feltz, Zeitschrift fuer Chemie, 1966, 6(8), p. 318.*

Jeung-Ho So et al., "A Convenient Synthesis of Solvated and Unsolvated Anhydrous Metal Chlorides via Dehydration of Metal Chloride Hydrates with Trimethylchlorosilane", Inorg. Chem., 1990, 29, 1592-1593.

* cited by examiner

*Primary Examiner* — Michael G Hartley
*Assistant Examiner* — Leah Schlientz
(74) *Attorney, Agent, or Firm* — Juliet A. Jones; Samuel L. Borkowsky

(57) ABSTRACT

Method of producing anhydrous thorium(IV) tetrahalide complexes, utilizing $Th(NO_3)_4(H_2O)_x$, where x is at least 4, as a reagent; method of producing thorium-containing complexes utilizing $ThCl_4(DME)_2$ as a precursor; method of producing purified $ThCl_4(ligand)_x$ compounds, where x is from 2 to 9; and novel compounds having the structures:

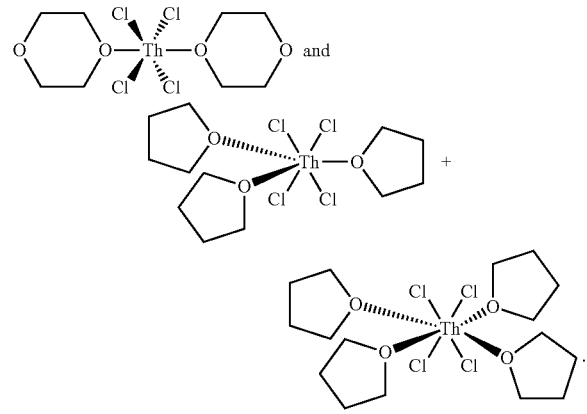

9 Claims, 1 Drawing Sheet

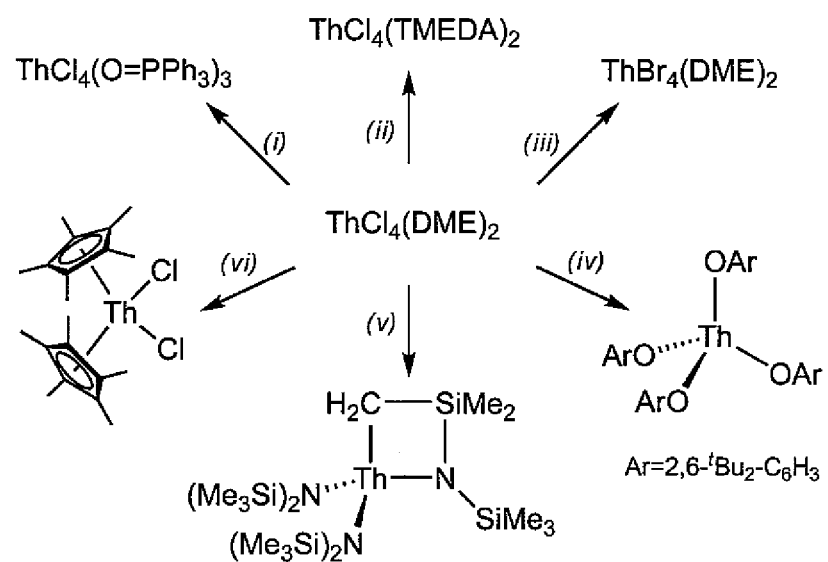

METHOD OF SYNTHESIS OF ANHYDROUS THORIUM(IV) COMPLEXES

STATEMENT OF FEDERAL RIGHTS

The United States government has rights in this invention pursuant to Contract No. DE-AC52-06NA25396 between the United States Department of Energy and Los Alamos National Security, LLC for the operation of Los Alamos National Laboratory.

FIELD OF THE INVENTION

The present invention relates to methods of synthesis of anhydrous thorium(IV) tetrahalide complexes, including $ThCl_4(DME)_2$, $ThCl_4(1,4\text{-dioxane})_2$, and $ThCl_4(THF)_x$, using $Th(NO_3)_4(H_2O)_x$ as a precursor, in high yield and under comparatively mild reaction conditions.

BACKGROUND OF THE INVENTION

Anhydrous halide complexes are key starting materials in the synthesis of transition metal, lanthanide and actinide complexes. For non-aqueous thorium chemistry, $ThBr_4(THF)_4$ and $ThCl_4$ have been the most commonly used precursors, but their syntheses suffer from several inconvenient drawbacks, which have, in turn, greatly hampered progress in thorium research. For example, the synthesis of $ThBr_4(THF)_4$ requires thorium(0) metal, a material which is both expensive and available at only a small number of institutions. Furthermore, synthesis of thorium(0) metal is highly dependent on the type of thorium metal used (e.g., turnings, powder or chips) and the complex is thermally sensitive with ring-opening and subsequent polymerization of THF being a problem. The synthetic procedures for $ThCl_4$ require special equipment and more dangerous protocols that involve elevated temperatures (300-500° C.). For example, one method involves reacting thorium dioxide or thoria ($ThO_2$) with $CCl_4$ vapor at 450-500° C. for several days, while another requires heating thorium metal with $NH_4Cl$ at 300° C. for 30 h to initially generate $(NH_4)_2ThCl_6$, which is then heated at 350° C. under high vacuum to ultimately give $ThCl_4$.

The increasing use of thorium in catalysis and materials science, coupled with the growing interest in developing a proliferation-resistant thorium nuclear fuel cycle, creates a need for straightforward access to anhydrous thorium(IV) starting materials.

SUMMARY OF THE INVENTION

The present invention meets the aforementioned need by describing novel methods of safer and more economically viable thorium(IV) halide syntheses, which share none of the disadvantages of previously available methods, e.g., are performed at lower temperatures, require shorter reaction periods and reproducibly result in high yields. The present invention utilizes thorium nitrate, $Th(NO_3)_4(H_2O)_x$, where x is at least 4, as a safe and economically viable starting material for the synthesis of thorium(IV) chloride hydrates. Anhydrous HCl and $Me_3SiCl$ serve as effective drying reagents in reactions that produce $ThCl_4(DME)_2$ and $ThCl_4(1,4\text{-dioxane})_2$. $ThCl_4(DME)_2$ may be used as a starting material in reactions to produce a number of useful products, as depicted in FIG. 1. Finally, $ThCl_4(1,4\text{-dioxane})_2$ may be easily converted to novel thorium complexes $ThCl_4(THF)_x$ in good yield and under mild reaction conditions.

The following describe some non-limiting embodiments of the present invention.

According to one embodiment of the present invention, a method of producing anhydrous thorium(IV) tetrahalide complexes is provided, comprising providing $Th(NO_3)_4(H_2O)_x$, where x is at least 4; reacting said $Th(NO_3)_4(H_2O)_5$ with a halide-containing strong acid to produce $ThX_4(H_2O)_4$, wherein X is a halide selected from the group consisting of bromide, chloride, iodide, and combinations thereof; and, drying the $ThX_4(H_2O)_4$ with $Me_3SiCl$ or a mixture of anhydrous HCl and $Me_3SiCl$ in a suitable solvent to produce a $ThX_4$-ligand complex.

According to another embodiment of the present invention, a method of producing thorium-containing complexes is provided, comprising providing $ThCl_4(\text{dimethoxyethane})_2$; and, reacting the $ThCl_4(\text{dimethoxyethane})_2$ with a suitable reagent to produce thorium(IV) complexes comprising thorium(IV)-oxygen bonds, thorium(IV)-nitrogen bonds, thorium(IV)-halide bonds, thorium(IV)-carbon bonds, and combinations thereof.

According to yet another embodiment of the present invention, a method of producing purified $ThCl_4(\text{ligand})_x$ compounds, where x=from 2 to 9, is provided, comprising providing $ThCl_4(1,4\text{-dioxane})_2$; and, reacting the $ThCl_4(1,4\text{-dioxane})_2$ with a suitable ligand donor to produce $ThCl_4(\text{ligand})_x$.

According to yet another embodiment of the present invention, a compound is provided comprising:

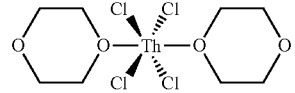

According to yet another embodiment of the present invention, a compound is provided comprising:

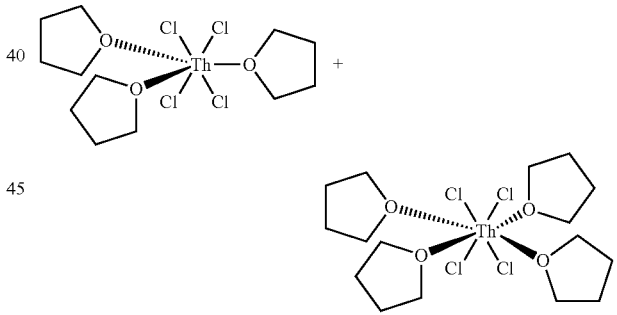

BRIEF DESCRIPTION OF THE DRAWINGS

FIG. 1 depicts non-limiting examples of reactions and products of $ThCl_4(DME)_2$. Reagents and conditions: (i) 3 equiv. $Ph_3P=O$, THF, 100% yield; (ii) excess TMEDA, THF, 100% yield; (iii) excess $Me_3SiBr$, toluene, 24 h, 100% yield; (iv) 4 equiv. KOAr (Ar=2,6-$^tBu_2$-$C_6H_3$), THF, 99% yield; (v) 4 equiv. $Na[N(SiMe_3)_2]$, toluene, reflux, 12 h, 93% yield; (vi) 2 equiv. $(C_5Me_5)MgCl.THF$, toluene, reflux, 24 h, 88% yield.

DETAILED DESCRIPTION OF THE INVENTION

The present invention relates to methods of producing a variety of thorium(IV) containing complexes. Herein, the terms complexes, adducts and compounds are used interchangeably.

Aspects of the present invention are described by Thibault Cantat, Brian L. Scott and Jaqueline L. Kiplinger in Chem. Commun., 2010, 46, pp. 919-921, incorporated herein by reference in its entirety.

One aspect of the present invention describes a method of producing anhydrous thorium(IV) tetrahalide complexes. The method uses $Th(NO_3)_4(H_2O)_5$ as a starting material, which is allowed to react with a halide-containing strong acid to produce $ThX_4(H_2O)_4$. In addition to thorium, other actinide nitrate compounds may be used as starting materials, including uranium, neptunium and plutonium nitrates. It also should be noted that the number of ($H_2O$) ligands in the starting material may vary. For example, $Th(NO_3)_4(H_2O)_x$ may be used, where x is at least 4, and in theory, has no upper limit. The halide in the strong acid may be bromide, chloride and/or iodide, and in one embodiment is chloride. Fluoride-containing acids are not considered suitable for use in the present invention, due to high reactivity and safety concerns. Upon formation of the $ThX_4(H_2O)_4$, the product is dried with a suitable drying agent in the presence of a solvent. Examples of suitable drying agents include, but are not limited to, $Me_3SiCl$ (chlorotrimethylsilane), $Me_3SiBr$ (bromotrimethylsilane), $Me_3SiI$ (iodotrimethylsilane), thionyl chloride ($SOCl_2$), and phosgene ($COCl_2$), to name a few. However, $Me_3SiCl$ has several advantages, such as not requiring extensive purification prior to use, shorter reaction times, lower temperatures, and fewer safety concerns. Thus, in one embodiment, the drying agent is $Me_3SiCl$. It is believed that the present invention describes for the first time that the combination of a strong acid such as HCl and $Me_3SiCl$ has been used to successfully dry wet compounds to produce anhydrous compounds.

The type of solvent determines which $ThX_4$-ligand complex is formed. Non-limiting examples of solvents that may be used include dimethoxyethane (DME), dioxanes (including 1,4-dioxane), pyridines, amines, ethers (oxygen, sulfur, selenium, tellurium), nitrites, isonitriles, ketones, aldehydes, phopshines, phosphine oxides, phosphine sulfides, phosphine selenides, phoephine tellurides, pyridine N-oxides, thiocarbamates, N-heterocyclic carbenes, thiols, alcohols, selenols, tellurols, isocyanates, thioisocyanates, heterocumulenes, sulfoxides, furans, and combinations thereof. In one embodiment, the solvent is selected from the group consisting of dimethoxyethane (DME), tetrahydrofuran (THF), 1,4-dioxane, and combinations thereof. When DME is used as a solvent, the $ThX_4$-ligand complex formed is $ThCl_4$(dimethoxyethane)$_2$, which has the following structure:

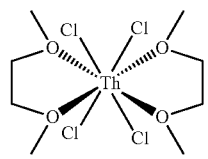

When a dioxane such as 1,4-dioxane is used, the novel compound $ThCl_4$(1,4-dioxane)$_2$ is, formed, which is useful, for among other things, as a reagent for producing heretofore difficult or impossible to produce $ThCl_4$ complexes. $ThCl_4$(1, 4-dioxane)$_2$ has the following structure:

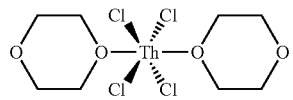

The reactions are performed at a temperature of 100° C. or less, for a period of about 12 hours or less. By means of example only, reaction (1) may be performed for about 6 hours, and reaction (2) may be performed for about 12 hours (see Example 1). The % yield, defined as the (mass of the product recovered from the reaction/the theoretical maximum mass of obtainable product)×100, is at least 90%.

Another aspect of the present invention provides a method of producing a variety of thorium-containing complexes, which prior to the present invention, had been extremely difficult to produce in purified form and in useful quantities (on the order of grams). When $ThCl_4(DME)_2$ is allowed to undergo a reaction with a variety of reagents, thorium(IV) complexes are produced which contain thorium(IV)-oxygen bonds, thorium(IV)-nitrogen bonds, thorium(IV)-halide bonds and/or thorium(IV)-carbon bonds, which are critical for developing routes to thorium-oxides, thorium-nitrides, thorium-carbides and sol-gel science for nuclear materials storage, processing, and fuel. These homogeneous thorium complexes will also be invaluable for grafting thorium onto solid supports for industrial or large scale applications and closing the thorium fuel cycle. FIG. 1 depicts the various thorium(IV) complexes that are produced, including thorium (IV) halide complexes, such as $ThBr_4$(dimethoxyethane)$_2$, $ThCl_4$(N,N'-tetramethylenediamine)$_2$, and $ThCl_4(O=PPh_3)_3$; thorium(IV) alkoxide complexes, such as $Th(O-2,6-^tBu_2-C_6H_3)_4$; thorium(IV) amide complexes, such as $[(Me_3Si)_2N]_2Th[\kappa^2-(C,N)-CH_2Si(CH_3)_2N(SiMe_3)]$; and thorium(IV) organometallic complexes, such as $(C_5Me_5)_2ThCl_2$ and $[(Me_3Si)_2N]_2Th[\kappa^2-(C,N)-0-11Si(CH_3)_2N(SiMe_3)]$. Suitable reagents include, but are not limited to, triphenylphosphine oxide, N,N'-tetramethylethylenediamine, bromotrimethylsilane, iodotrimethylsilane, potassium 2,6-di-tert-butylphenoxide, sodium hexamethyldisilazide, $(C_5Me_5)$MgCl.THF, and combinations thereof. The complexes typically are produced in a yield of at least 80%, and have a purity of at least 90%, alternatively of at least 95%, and alternatively of at least 99%.

Another aspect of the present invention provides a method for producing purified $ThCl_4$(ligand)$_x$, complexes, wherein x is from 2 to 9, and alternatively from 3 to 4, and alternatively is 3.5. In this method, $ThCl_4$(1,4-dioxane)$_2$ is used as a starting material and allowed to react with a suitable ligand donor. One non-limiting example of a suitable donor is tetrahydrofuran (THF), which results in $ThCl_4(THF)_{3.5}$, having the following structure:

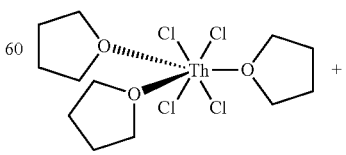 +

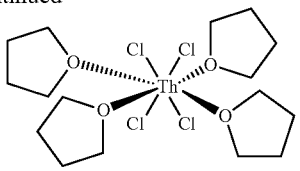

The significance of this aspect lies in the fact that ThCl$_4$(THF)$_{1.5}$ is extremely useful as a starting material in non-aqueous thorium complexes, and prior to this work has not been possible to produce in useful, purified quantities (e.g., in gram quantities). As has been described previously in the literature, coordination of THF to an electrophilic actinide metal center leads to ring-opening following nucleophilic attack from another molecule of THF, which leads to THF polymerization. This results in essentially no yield of ThCl$_4$-THF complexes, and any that is produced cannot be separated from the polymeric matrix. Conversion of ThCl$_4$(1,4-dioxane)$_2$ to ThCl$_4$(THF)$_{3.5}$ occurs in a yield of at least 90%, and may be greater than 99%.

Finally, both ThCl$_4$(1,4-dioxane)$_2$ and ThCl$_4$(THF)$_{3.5}$ can be converted to ThCl$_4$(DME)$_2$Thus, both are useful precursors for the synthesis of thorium halide, alkoxide, amide and organometallic compounds.

EXAMPLES

General Synthetic Considerations

Unless otherwise noted, all reactions and manipulations were performed at 20° C. in a recirculating Vacuum Atmospheres NEXUS Model inert atmosphere (N$_2$) drybox equipped with a 40CFM Dual Purifier NI-Train. Glassware was dried overnight at 150° C. before use. All NMR spectra were obtained using a Bruker Avance 300 MHz spectrometer. Chemical shifts for $^1$H and $^{13}$C {$^1$H} NMR spectra were referenced to solvent impurities. Elemental analyses (C, H, Cl and Th) were performed at Columbia Analytical Services in Tucson and Phoenix, Ariz. X-ray data were collected using a Bruker APEX2 diffractometer. Structural solution and refinement was achieved using the SHELXL program suite, i.e., Bruker, APEX2 1.08, APEX2 Data Collection Software; Bruker Analytical X-ray Systems: Madison, Wis., 2003; Bruker, SAINT+ 7.06, Integration Software; Bruker Analytical X-ray Systems: Madison, Wis., 2001; Sheldrick, G. M. SADABS 2.03, Program for Adsorption Correction; University of Göttingen: Göttingen, Germany, 2001; Sheldrick, G. M. SHELXS-97 and SHELXL-97, Structure Solution and Refinement Package; Universitiy of Göttingen: Göttingen, Germany, 1997; Bruker, SHELXTL 6.10, Molecular Graphics and Publication Software Package; Bruker Analytical X-ray Systems: Madison, Wis., 2000. Details regarding data collection are provided in the CIF files which can be found at DOI: 10.1039/b923558b.

Unless otherwise noted, reagents were purchased from commercial suppliers and used without further purification. Celite (Aldrich), alumina (Brockman I, Aldrich) and 4 Å molecular sieves (Aldrich) were dried under dynamic vacuum at 250° C. for 48 h prior to use. All solvents (Aldrich) were purchased anhydrous, dried over KH for 24 h, passed through a column of activated alumina, and stored over activated 4 Å molecular sieves prior to use. Benzene-d$_6$ (Aldrich) and tetrahydrofuran-d$_8$ (Cambridge Isotope Laboratories) were purified by storage over activated 4 Å molecular sieves or sodium metal prior to use. Th(NO$_3$)$_4$(H$_2$O)$_5$ was purchased from Merck. Triphenylphosphine oxide, Na[N(SiMe$_3$)$_2$], Me$_3$SiCl, Me$_3$SiBr, concentrated HCl (37 wt. % in H$_2$O, 12 M), HCl/diethyl ether (2.0M) were purchased from Aldrich. (C$_5$Me$_5$)MgCl.THF and K(O-2,6-$^t$Bu$_2$-C$_6$H$_3$) were prepared according to literature procedures. Caution: Natural thorium (primary isotope in') is a weak alpha-emitter (4.012 MeV) with a half-life of 1.41×10$^{10}$ years; manipulations and reactions should be carried out in monitored fume hoods or in an inert atmosphere drybox in a radiation laboratory equipped with alpha- and beta-counting equipment.

Example 1

As shown in eqn (1), quantitative conversion of Th(NO$_3$)$_4$(H$_2$O)$_5$ into the thorium(IV) chloride tetrahydrate complex ThCl$_4$(H$_2$O)$_4$ was achieved by refluxing Th(NO$_3$)$_4$(H$_2$O)$_5$ in concentrated aqueous HCl (12 M) solution. ThCl$_4$(H$_2$O)$_4$ is a white solid, and is insoluble in hydrocarbons but soluble in tetrahydrofuran (THF), dimethoxyethane (DME) and 1,4-dioxane. Confirmation of a tetrahydrate form was determined by elemental analysis, as well as recrystallization from THF or 1,4-dioxane, which produced ThCl$_4$(H$_2$O)$_4$.(THF)$_5$ and ThCl$_4$(H$_2$O)$_4$.(1,4-dioxane)$_3$, respectively.

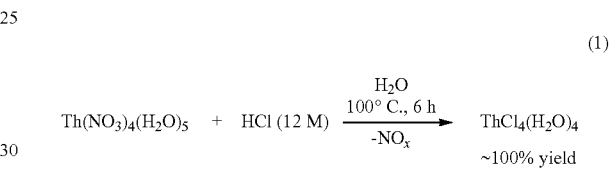

(1)

Me$_3$SiCl was used as a drying reagent for ThCl$_4$(H$_2$O)$_4$. Unfortunately, reaction between ThCl$_4$(H$_2$O)$_4$ and Me$_3$SiCl in THF resulted in THF polymerization, which precluded the isolation of a thorium compound. The same reaction was performed in the presence of an excess of anhydrous HCl (2.0 M/diethyl ether). Under these conditions, the monohydrate complex ThCl$_4$(H$_2$O)(THF)$_3$ formed rapidly; however, removal of the residual H$_2$O results in THF polymerization. Replacing THF by DME as a solvent, however, resulted in successful dehydration of ThCl$_4$(H$_2$O)$_4$ using Me$_3$SiCl (eqn (2)). The reaction is complete after 12 h at 90° C. and ThCl$_4$(DME)$_2$ is easily isolated in nearly quantitative yield (95%) after precipitation with hexane. ThCl$_4$(DME)$_2$ was characterized by a combination of $^1$H and $^{13}$C{$^1$H} NMR spectroscopy, elemental analysis and X-ray crystallography.

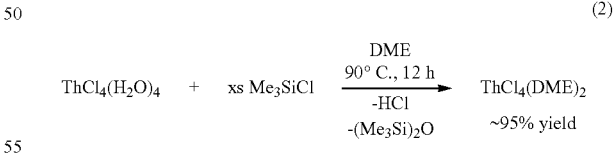

(2)

Synthesis of ThCl$_4$(H$_2$O)$_4$

A 500-mL round-bottom flask was charged with thorium nitrate Th(NO$_3$)$_4$(H$_2$O)$_5$ (20.0 g, 35.1 mmol) and a magnetic stir bar. The solid was then dissolved in concentrated HCl (100 mL) with stirring. In a well-ventilated fume hood, the resulting solution was refluxed for 6 h until no evolution of orange-colored gas was observed and the reaction mixture was colorless (Caution! Nitrogen oxides are toxic and hazardous gases). Volatiles were removed under reduced pressure to afford ThCl$_4$(H$_2$O)$_4$ as a white solid (8.1 g, 18.1 mmol, 100%). $^1$H NMR (THF-d$_5$, 298 K): δ 7.17 (bs, v$_{1/2}$=47 Hz;

H$_2$O). Anal. Calcd. for Cl$_4$H$_8$O$_4$Th (mol. wt. 445.91): C, 0.00; H, 1.81. Found: C, <0.2 (not detected); H, 1.56.

Synthesis of ThCl$_4$(DME)$_2$

A 500-mL round-bottom Schlenk flask equipped with a magnetic stir bar was charged with ThCl$_4$(H$_2$O)$_4$ (15.5 g, 34.8 mmol). The solid was dissolved in DME (100 mL) under an argon flow. Using an addition funnel, Me$_3$SiCl (70 mL, 557 mmol) was added dropwise at room temperature as the reaction is exothermic; upon addition, a crystalline white precipitate forms. The reaction vessel was sealed and the mixture was stirred for 12 h in an 50° C. oil bath. The volume was then concentrated to 20 mL under reduced pressure, leaving a white suspension. The reaction vessel is brought into a drybox. Addition of hexanes (50 mL), followed by filtration over a coarse-porosity fritted filter and drying under reduced pressure afforded ThCl$_4$(DME)$_2$ as a white solid (18.3 g, 33.1 mmol, 95%). $^1$H NMR(C$_6$D$_6$, 298K): δ 3.76 (s, 6H; OCH$_3$), 3.33 ppm (s, 4H; OCH$_2$). $^{13}$C{$^1$H} NMR(C$_6$D$_6$, 298K): δ 73.6 (s), 65.8 ppm (s). Anal. Calcd. for C$_8$H$_{20}$Cl$_4$O$_4$Th (mol. wt. 554.09): C, 17.34; H, 3.64. Found: C, 17.38; H, 3.63.

Example 2

ThCl$_4$(DME)$_2$ proved to be an excellent synthetic precursor to a wide range of thorium(IV) halide, alkoxide, amide and organometallic complexes, as outlined in FIG. 1. Displacement of the DME ligands by monodentate ligands such as triphenylphosphine oxide (O=PPh$_3$) or bidentate ligands such as N,N-tetramethylethylenediamine (TMEDA) resulted in the complexes ThCl$_4$(O=PPh$_3$)$_3$ and ThCl$_4$(TMEDA)$_2$. Transmetallation chemistry using excess bromotrimethylsilane (Me$_3$SiBr) smoothly converted ThCl$_4$(DME)$_2$ to ThBr$_4$(DME)$_2$. Salt metathesis between 4 equiv. potassium 2,6-di-tert-butylphenoxide and ThCl$_4$(DME)$_2$ quantitatively afforded the homoleptic alkoxide complex Th(O-2,6-$^t$Bu-C$_6$H$_3$)$_4$. Similarly, reaction of 4 equiv. sodium hexamethyldisilazide with ThCl$_4$(DME)$_2$ yielded the known cyclometallated [(Me$_3$Si)$_2$N]$_2$Th[κ$^2$-(C,N)—CH$_2$Si(CH$_3$)$_2$N(SiMe$_3$)] complex in approximately 93% yield. Finally, the bis(pentamethylcyclopentadienyl) complex (C$_5$Me$_5$)$_2$ThCl$_2$ was prepared in approximately 88% yield from ThCl$_4$(DME)$_2$ and 2 equiv. (C$_5$Me$_5$)MgCl.THF. Overall, the reaction chemistry with ThCl$_4$(DME)$_2$ has been performed to produce multi-gram quantities in high yields (e.g., greater than 88%).

Synthesis of ThCl$_4$(O=PPh$_3$)$_3$

A 125-mL sidearm flask was charged with a magnetic stir bar, ThCl$_4$(DME)$_2$ (1.40 g, 2.52 mmol), triphenylphosphine oxide (2.10 g, 7.55 mmol) and THF (30 mL). The reaction mixture was stirred at room temperature for 6 h. The volatiles were then removed under reduced pressure to give ThCl$_4$(O=PPh$_3$)$_3$ as a white solid (3.05 g, 2.52 mmol, 100%). $^1$H NMR (THF-d$_5$, 298K): δ 7.83 (bs, 18H; Ph), 7.53 (bs, 9H; Ph), 7.43 (bs, 18H; Ph).

Synthesis of ThCl$_4$(TMEDA)$_2$

A 20-mL scintillation vial was charged with a stir bar, ThCl$_4$(DME)$_2$ (0.280 g, 0.505 mmol) and THF (3 mL). To the resulting solution, TMEDA (100 μL, 0.667 mmol) was added using a syringe. The reaction mixture was stirred at room temperature for 30 min. The volatiles were then removed under reduced pressure to give ThCl$_4$(TMEDA)$_2$ as a white solid (0.306 g, 0.505 mmol, 100%). The $^1$H NMR spectrum collected in C$_6$D$_6$ was consistent with the data previously reported for ThCl$_4$(TMEDA)$_2$.

Synthesis of ThBr$_4$(DME)$_2$

A 20-mL scintillation vial was charged with a stir bar, ThCl$_4$(DME)$_2$ (0.280 g, 0.505 mmol) and toluene (3 mL). To the resulting solution, Me$_3$SiBr (330 μL, 2.50 mmol) was added using a syringe. The reaction mixture was stirred at room temperature for 48 h. The volatiles were then removed under reduced pressure to give ThBr$_4$(DME)$_2$ as a white solid (0.369 g, 0.505 mmol, 100%). The $^1$H NMR spectrum collected in C$_6$D$_6$ is consistent with the data previously reported for complex ThBr$_4$(DME)$_2$.

Synthesis of Th(O-2,6$^t$Bu$_2$-C$_6$H$_3$)$_4$

In a drybox, a 250-mL sidearm flask equipped with a stir bar was charged with ThCl$_4$(DME)$_2$ (5.30 g, 9.57 mmol) and THF (15 mL). A THF (100 mL) solution of potassium 2,6-di-tert-butylphenoxide (9.59 g, 39.2 mmol) was added dropwise at room temperature. The reaction mixture was stirred for 3 h and then filtered through a Celite-padded coarse-porosity fritted filter. The volatiles were removed under reduced pressure and the resulting off-white solid extracted into 100 mL hot (60° C.) toluene. The solution was collected and the volatile removed under reduced pressure to give Th(O-2,6-$^t$Bu$_2$-C$_6$H$_3$)$_4$ as a white solid (9.98 g, 9.47 mmol, 99%). $^1$H and $^{13}$C{$^1$H} NMR spectra collected in C$_6$D$_6$ were consistent with the data previously reported for Th(O-2, 6$^t$Bu$_2$-C$_6$H$_3$)$_4$.

Synthesis of [(Me$_3$Si)$_2$N]$_2$Th[κ$^2$-(N,C)—CH$_2$Si(CH$_3$)$_2$N(SiMe$_3$)]

In a drybox, a 250-mL Schlenk flask equipped with a stir bar was charged with ThCl$_4$(DME)$_2$ (4.76 g, 86.0 mmol), Na[N(SiMe$_3$)$_2$] (6.30 g, 34.4 mmol) and toluene (100 mL). The reaction vessel was sealed, transferred to a fume hood, and heated in a 110° C. oil bath for 24 h. The volatiles were then removed under reduced pressure and the resulting white solid was extracted with 60 mL hexane and filtered through a Celite-padded coarse-porosity flitted filter. The volume of the collected filtrate was reduced to 10 mL and (Me$_3$Si)$_2$O (50 mL) was added. The resulting white suspension was cooled to −35° C., filtered using a fine-porosity fritted filter, and dried under reduced pressure to give [(Me$_3$Si)$_2$N]$_2$Th[κ$^2$-(N,C)—CH$_2$Si(CH$_3$)$_2$N(SiMe$_3$)] as a white solid (5.69 g, 7.99 mmol, 93%). The $^1$H NMR spectrum collected in C$_6$D$_6$ was consistent with the data previously reported for [(Me$_3$Si)$_2$N]$_2$Th[κ$^2$-(N,C)—CH$_2$Si(CH$_3$)$_2$N(SiMe$_3$)].

Synthesis of (C$_5$Me$_5$)$_2$ThCl$_2$

A 250-mL round-bottom Schlenk flask equipped with a magnetic stir bar was charged with ThCl$_4$(DME)$_2$ (5.37 g, 9.70 mmol), (C$_5$Me$_5$)MgCl.THF (5.70 g, 21.3 mmol) and toluene (70 mL). The reaction vessel was sealed, transferred to a hood, and heated in an 100° C. oil bath for 48 h with stirring. The reaction mixture was cooled to ambient temperature and transferred to a drybox. The solution was heated and filtered while hot through a Celite-padded coarse-porosity fitted filter. The solid collected was washed with 15 mL hot (100° C.) toluene and dried under reduced pressure to give as a white solid (C$_5$Me$_5$)$_2$ThCl$_2$ (4.89 g, 8.54 mmol, 88%). The $^1$H NMR spectrum collected in C$_6$D$_6$ was consistent with the data previously reported for (C$_5$Me$_5$)$_2$ThCl$_2$.

Example 3

Despite its great synthetic profile, the DME ligand in ThCl$_4$(DME)$_2$ is not displaced by weak donor ligands such as THF. To prevent this from being an issue, other donors were examined as alternatives to DME. The insolubility of ThCl$_4$(H$_2$O)$_4$ in most organic solvents precluded its reaction with Me$_3$SiCl. Although ThCl$_4$(H$_2$O)$_4$ is fairly soluble in 1,4-dioxane, no reaction was observed with Me$_3$SiCl, even after several days at 150° C. However, addition of anhydrous HCl (2.0 M/diethyl ether) to the reaction medium leads to the quantitative formation of the novel thorium(IV) tetrachloride complex ThCl$_4$(1,4-dioxane)$_2$ after 12 h at 130° C. (eqn (3)). The insolubility of ThCl$_4$(1,4-dioxane)$_2$ in non-coordinating solvents did not permit its characterization using NMR spectroscopy; however, its identity as ThCl$_4$(1,4-dioxane)$_2$ was confirmed by elemental analysis. Although only poor quality crystallographic data could be obtained for ThCl$_4$(1,4-dioxane)$_2$, connectivity was established and showed bridging 1,4-dioxane ligands, leading to the formation of an extended polymeric structure. This observation accounts for the apparent low coordination number of 6 suggested by the stoichiometry in ThCl$_4$(1,4-dioxane)$_2$.

In contrast to the DME ligands in ThCl$_4$(DME)$_2$, the 1,4-dioxane ligands in ThCl$_4$(1,4-dioxane)$_2$ are easily displaced by THF, leading to the novel complex ThCl$_4$(THF)$_3$.5 (eqn (4)), which was fully characterized using $^1$H NMR spectroscopy and elemental analysis. Whereas the dioxane adduct is stable in solution and in the solid state at 130° C., the THF adduct ThCl$_4$(THF)$_{3.5}$ is thermally sensitive and eventually undergoes THF ring-opening at room temperature. It is remarkable that this new route permits access to the THF adduct, whereas direct synthesis from ThCl$_4$(H$_2$O)$_4$ systematically failed. This clearly establishes the synthetic utility of the dioxane adduct. Both the dioxane and the THF adducts are easily converted to ThCl$_4$(DME)$_2$ by reaction with DME (eqn (5)).

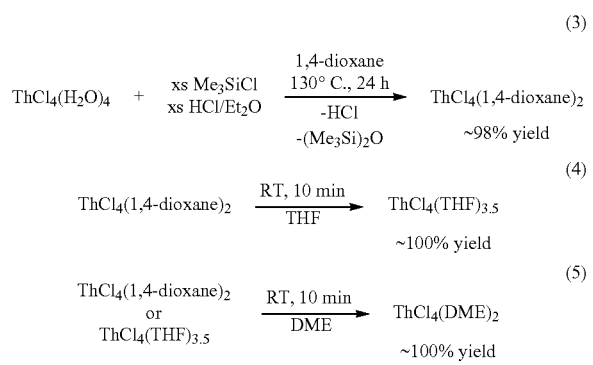

Synthesis of ThCl$_4$(1,4-dioxane)$_2$

In a drybox, a 20-mL thick-walled Schlenk tube equipped with a Teflon valve and a stir bar was charged with ThCl$_4$(H$_2$O)$_4$ (1.30 g, 2.92 mmol). Next, 1,4-dioxane (4.0 mL), TMSCl (4.0 mL, 31.6 mmol) and a solution of HCl/diethyl ether (4.0 mL, 2.0 M, 8.0 mmol) were added using a syringe. The reaction vessel was sealed and the reaction mixture stirred for 15 h in a 130° C. oil bath. The reaction mixture was then cooled to ambient temperature and tranferred to a drybox. The solution was concentrated to half its original volume (~6 mL) and hexane (15 mL) was added. The resulting white suspension was collected over a fine-porosity fritted filter and dried under reduced pressure to give ThCl$_4$(1,4-dioxane)$_2$ as a white solid (1.57 g, 2.86 mmol, 98%). The insolubility of ThCl$_4$(1,4-dioxane)$_2$ in noncoordinating solvents precluded its characterization using NMR spectroscopy. Dissolution of ThCl$_4$(1,4-dioxane)$_2$ in coordinating solvents (such as THF) leads to the displacement of the 1,4-dioxane ligands. Anal. Calcd. for C$_8$H$_{16}$Cl$_4$O$_4$Th (mol. wt. 550.06): C, 17.47; H, 2.93; Cl, 25.78; Th, 42.18. Found: C, 17.57; H, 2.63; Cl, 26.0; Th, 38.5.

Synthesis of ThCl$_4$(THF)$_{3.5}$

A 20-mL scintillation vial was charged with ThCl$_4$(1,4-dioxane)$_2$ (0.500 g, 0.909 mmol) and THF (5 mL). The resulting solution was stirred at room temperature for 10 minutes. The volatiles were removed under reduced pressure affording ThCl$_4$(THF)$_3$.5 as a white solid (0.569 g, 0.909 mmol, 100%). $^1$H NMR(C$_6$D$_6$, 298K): δ 3.98 (s, 4H; CH$_2$O), 1.28 ppm (s, 4H; CH$_2$CH$_2$O). Anal. Calcd. for C$_{14}$H$_{28}$Cl$_4$O$_{3.5}$Th (mol. wt. 626.22): C, 26.85; H, 4.51; Cl, 22.65. Found: C, 27.03; H, 4.53; Cl, 23.0.

In all embodiments of the present invention, all percentages are by weight of the total composition, unless specifically stated otherwise. All ratios are weight ratios, unless specifically stated otherwise. All ranges are inclusive and combinable. All numerical amounts are understood to be modified by the word "about" unless otherwise specifically indicated. All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

Whereas particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of producing anhydrous thorium(IV) tetrahalide complexes comprising:
    a) providing Th(NO$_3$)$_4$(H$_2$O)$_x$, where x is at least 4;
    b) reacting said Th(NO$_3$)$_4$(H$_2$O)$_x$ with a halide-containing strong acid to produce ThX$_4$(H$_2$O)$_4$, wherein X is a halide selected from the group consisting of bromide, chloride, iodide, and combinations thereof; and,
    c) drying the ThX$_4$(H$_2$O)$_4$ with Me$_3$SiCl or a mixture of anhydrous HCl and Me$_3$SiCl in a suitable solvent to produce a ThX$_4$-ligand complex of the formula ThX$_4$(ligand)$_2$, wherein a molecule of ligand is a molecule of the suitable solvent, the suitable solvent selected from the group consisting of dimethoxyethane and dioxane.

2. The method of claim 1, wherein X is chloride.

3. The method of claim 1, wherein the solvent is dimethoxyethane.

4. The method of claim 3, wherein the ThX$_4$-ligand complex is ThCl$_4$(dimethoxyethane)$_2$.

5. The method of claim 1, wherein the solvent is a dioxane.

6. The method of claim 5, wherein the ThX$_4$-ligand complex is ThCl$_4$(1,4-dioxane)$_2$.

7. The method of claim 1, wherein the ThX$_4$-ligand complex is present in a yield of at least 90%.

8. The method of claim 1, wherein the reaction is performed at a temperature of 130° C. or less.

9. A compound having the structure:

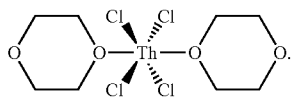

* * * * *